United States Patent [19]

Diana et al.

[11] Patent Number: 4,861,791
[45] Date of Patent: Aug. 29, 1989

[54] DIHYDRO-OXAZOLYL SUBSTITUTED-PHENYL-ALIPHATIC LOWER ALKYL AND THEIR USE AS ANTIVIRAL AGENTS

[75] Inventors: Guy D. Diana, Stephentown; Philip M. Carabateas, Schodack, both of N.Y.

[73] Assignee: Sterling Drug Inc., New York, N.Y.

[21] Appl. No.: 128,251

[22] Filed: Dec. 3, 1987

Related U.S. Application Data

[63] Continuation-in-part of Ser. No. 751,348, Jul. 2, 1985, abandoned, which is a continuation-in-part of Ser. No. 624,302, Jun. 25, 1984, abandoned, which is a continuation-in-part of Ser. No. 527,583, Aug. 29, 1983, abandoned.

[51] Int. Cl.$^4$ .................. A61K 31/42; C07D 413/10; C07D 413/12
[52] U.S. Cl. .................. 514/374; 514/326; 514/228.8; 514/236.8; 544/96; 544/137; 546/209; 548/143; 548/179; 548/205; 548/224; 548/237; 548/146; 548/235; 548/236
[58] Field of Search .................. 514/374; 548/237

[56] References Cited

U.S. PATENT DOCUMENTS

| | | | |
|---|---|---|---|
| 3,945,998 | 3/1976 | Anderson | 548/237 |
| 4,268,678 | 5/1981 | Diana et al. | 548/247 |
| 4,615,725 | 10/1986 | Weissmüller | 514/326 |

FOREIGN PATENT DOCUMENTS

| | | | |
|---|---|---|---|
| 2043188 | 3/1972 | Fed. Rep. of Germany | 514/376 |
| 46-21866 | 6/1971 | Japan | 514/374 |
| 757999 | 9/1956 | United Kingdom | 514/374 |

OTHER PUBLICATIONS

Henry et al., (1973) J. Med. Chem., 16(11), pp. 1287–1291.
R. J. Ash et al., Antimicrobial Agents and Chemotherapy 16, 301–305 (1979).

Primary Examiner—Donald G. Daus
Attorney, Agent, or Firm—Thomas L. Johnson; Paul E. Dupont

[57] ABSTRACT

Compounds of the formula

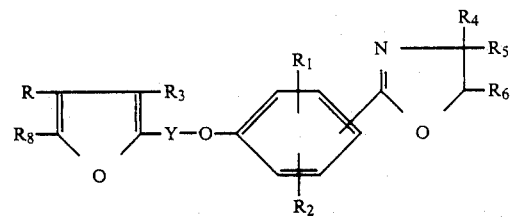

wherein the substituents are as defined herein are useful as antiviral agents, in particular against picornaviruses.

10 Claims, No Drawings

1

DIHYDRO-OXAZOLYL SUBSTITUTED-PHENYL-ALIPHATIC LOWER ALKYL AND THEIR USE AS ANTIVIRAL AGENTS

This application is a continuation-in-part of application Ser. No. 751,348, filed July 2, 1985, now abandoned, in turn a continuation-in-part of application Ser. No. 624,301, filed June 25, 1984, now abandoned, in turn a continuation-in-part of application Ser. No. 527,583, filed Aug. 29, 1983, now abandoned.

BACKGROUND OF THE INVENTION (a) Field of the Invention

This invention relates to novel heterocyclic substituted-phenyl-aliphatic-lower-alkylisoxazoles and furanes and to compositions and methods for the use thereof as antiviral agents.

(b) Information Disclosure Statement

Diana and Carabateas U.S. Pat. No. 4,268,678, issued May 19, 1981, discloses antivirally active compounds having the formula:

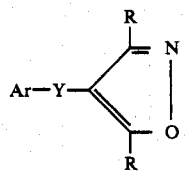

wherein Ar is phenyl substituted by one or two substituents selected from the group consisting of halogen, lower-alkoxy, nitro and hydroxy; Y is $(CH_2)_n$ or $O(CH_2)_n$ where n is an integer from 1 to 8; and R is lower-alkyl.

R. J. Ash et al., Antimicrobial Agents and Chemotherapy 16, 301–305 (1979) disclose the in vitro antirhinovirus activity of 1-[5-tetradecyloxy-2-furanyl]ethanone.

SUMMARY OF THE INVENTION

In a composition of matter aspect, the invention relates to compounds having the formulas:

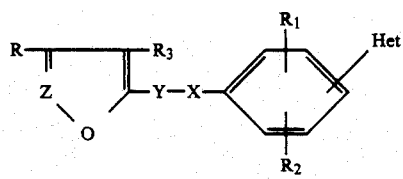

and

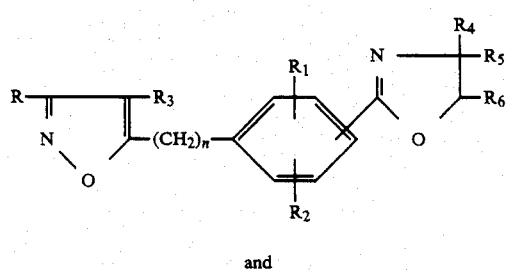

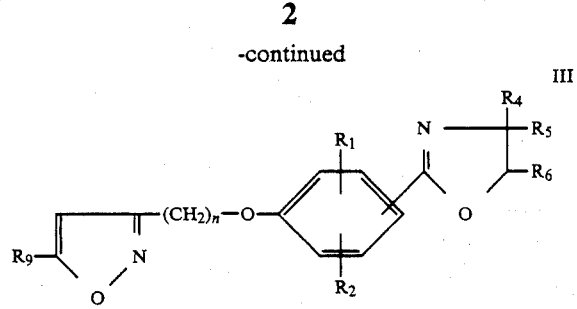

wherein:

Het in Formula I and the oxazolinyl ring in Formulas II and III are in the meta or para position with respect to the phenoxy or phenylalkyl linkage, and Het is selected from the group consisting of:

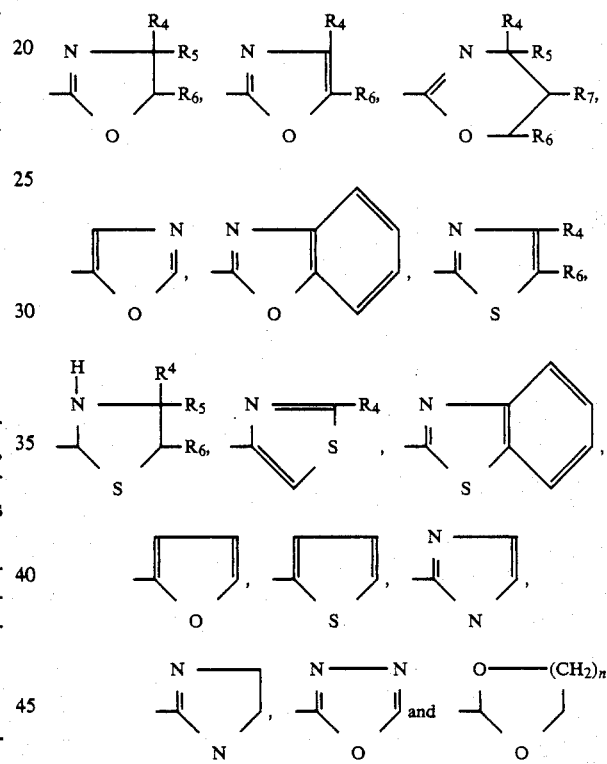

where
n' is 2 or 3;
Y is an alkylene bridge of 3 to 9 carbon atoms optionally interrupted by one or two oxygen atoms, by cyclohexyl or by an olefinic linkage;
X is O, S, SO or $SO_2$;
n is an integer from 3 to 9;
Z is N or $R_8C$, where $R_8$ is hydrogen or lower-alkanoyl;
$R_1$ and $R_2$ are selected from the group consisting of hydrogen, lower-alkyl, lower-alkenyl, halogen, nitro, lower-alkoxy, lower-alkylthio, difluoromethyl, trifuloromethyl, amino, lower-alkanoylamino, di-lower-alkylamino, hydroxy, lower-alkenoyl, lower-alkanoyl, hydroxymethyl and carboxy;
R, $R_3$, $R_4$, $R_5$, $R_6$ and $R_7$ are each hydrogen or alkyl of 1 to 3 carbon atoms optionally substituted by a member of the group consisting of hydroxy, lower-alkanoyloxy, lower-alkoxy, halo or N=Z', wherein N=Z' is amino, lower-alkanoylamino, lower-alkylamino, di-lower-alkylamino, 1-pyrrolidyl, 1-piperidinyl or 4-morpholinyl; with the proviso that when Z is N, R is other than hydrogen; and R₉ is alkyl of 1 to 3 carbon atoms;

or pharmaceutically acceptable acid-addition salts of basic members thereof.

A particular aspect of the invention relates to compounds of Formula I where Z is R₈C, X is O and Het is 4,5-dihydro-2-oxazolyl, viz.:

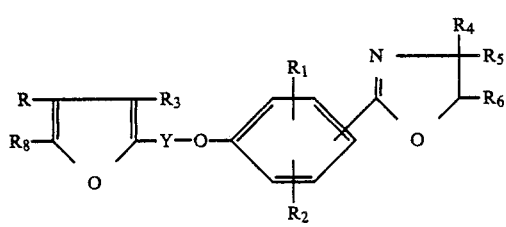

IA wherein R, R₃, R₄, R₅ and R₆ are each hydrogen or alkyl or hydroxyalkyl of 1–3 carbon atoms; and Y, R₁, R₂ and R₈ have the meanings given above.

In a further composition of matter aspect, the invention relates to compositions for combatting viruses which comprise an antivirally effective amount of a compound of Formulas I, II or III in admixture with a suitable carrier or diluent.

In a process aspect, the invention relates to a method for combatting viruses which comprises contacting the locus of such viruses with a composition containing an antivirally effective amount of a compound of Formulas I, II or III.

DETAILED DESCRIPTION INCLUSIVE OF PREFERRED EMBODIMENTS

The compounds of Formulas II and III and of Formula I where Het is a nitrogen-containing heterocyclic group, especially those where Het is an oxazolinyl or oxazolyl group, are sufficiently basic to form stable acid-addition salts with strong acids, and said salts are within the purview of the invention. The nature of the acid-addition salt is immaterial, provided it is derived from an acid the anion of which is essentially non-toxic to animal organisms. Examples of appropriate acid-addition salts include the hydrochloride, hydrobromide, sulfate, acid sulfate, maleate, citrate, tartrate, methanesulfonate, p-toluenesulfonate, dodecyl sulfate, cyclohexanesulfamate, and the like.

Throughout this sepecification, when the terms lower-alkyl, lower-alkenyl, lower-alkoxy, lower-alkanoyl, lower-alkanoyloxy, lower-alkylthio, lower-alkenoyl, lower-alkanoylamino, lower-alkylamino, and di-lower-alkylamino are used, they refer to such groups having from one to four carbon atoms. When the term halogen is used to define the substituents R₁ and R₂, any of the four common halogens, fluorine, chlorine, bromine or iodine are contemplated.

The compounds of Formula I wherein X is O are prepared by reacting a compound of the formula

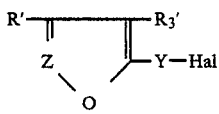

V wherein R' and R₃' are each hydrogen, or alkyl or hydroxyalkyl of 1 to 3 carbon atoms, R' being other than hydrogen when Z is N; Hal is chlorine, bromine or iodine; and Z and Y have the meanings given above, with an alkali metal salt of a compound of the formula

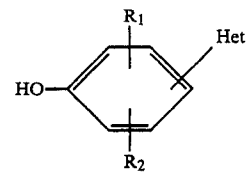

VI where R₁, R₂ and Het have the meanings given above. The reaction takes place by heating the reactants in an inert solvent in the presence of an alkali metal base, e.g. potassium carbonate at a temperature between about 50° and 150° C.

The intermediates of Formula V where Z is N are prepared by reacting an alkali metal derivative of an isoxazole of the formula

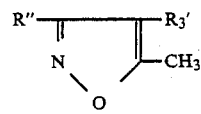

VII wherein R" is alkyl or hydroxyalkyl of 1 to 3 carbon atoms with a dihalide, Hal—Y'—Hal, where Y' is an alkylene bridge of 2 to 8 cabon atoms optionally interrupted by one or two oxygen atoms or by an olefinic linkage. Said alkali metal derivative is prepared in situ by treating the compound of Formula VII with an organo-alkali metal base under anhydrous conditions. Preferred organo-alkali metal bases are butyllithium and lithium diisopropylamide.

The intermediates of Formula V where Z is R₈C are prepared from the appropriate omega-(2-furan)alkanoic acid by reduction to the corresponding alcohol and replacement of the hydroxy group by halogen.

The intermediates of Formula VI are a generically known class of heterocyclic substituted phenols, prepared as described hereinafter in the general description and specific examples.

An alternative approach to the compounds of Formula I where Z is N and X is O is by the process of reacting a compound of the formula

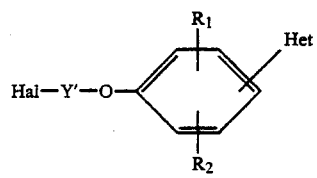

VIII where Hal is chlorine, bromine or iodine; Y' is an alkylene bridge of 2 to 8 carbon atoms optionally interrupted by one or two oxygen atoms or by an olefinic linkage; and R₁, R₂ and Het have the meanings given above, with an alkali metal derivative of a compound of Formula VII above.

A preferred class of compounds within the scope of Formula I are those where Z is N, X is O and Het is an oxazolinyl group, having the formula

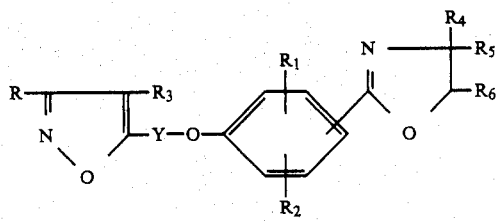

Intermediates for the compounds of Formula IX are conveniently prepared according to the following flow sheet.

XVII. The latter reacts with an alkali metal derivative of an isoxazole of Formula VII to give a compound of Formula IX.

In an alternative approach, the ester X is converted to the amide XV and the latter cyclized to a phenolic dihydro-oxazole (XVI). Etherification with an alkylene dibromide then gives XVII. The ether XVII, upon reaction with an intermediate of Formula V where Z is N, produces a compound of Formula IX.

The structures of the compounds of the invention were established by the modes of synthesis, by elementary analysis, and by infrared and nuclear magnetic resonance spectra.

The following examples will further illustrate the

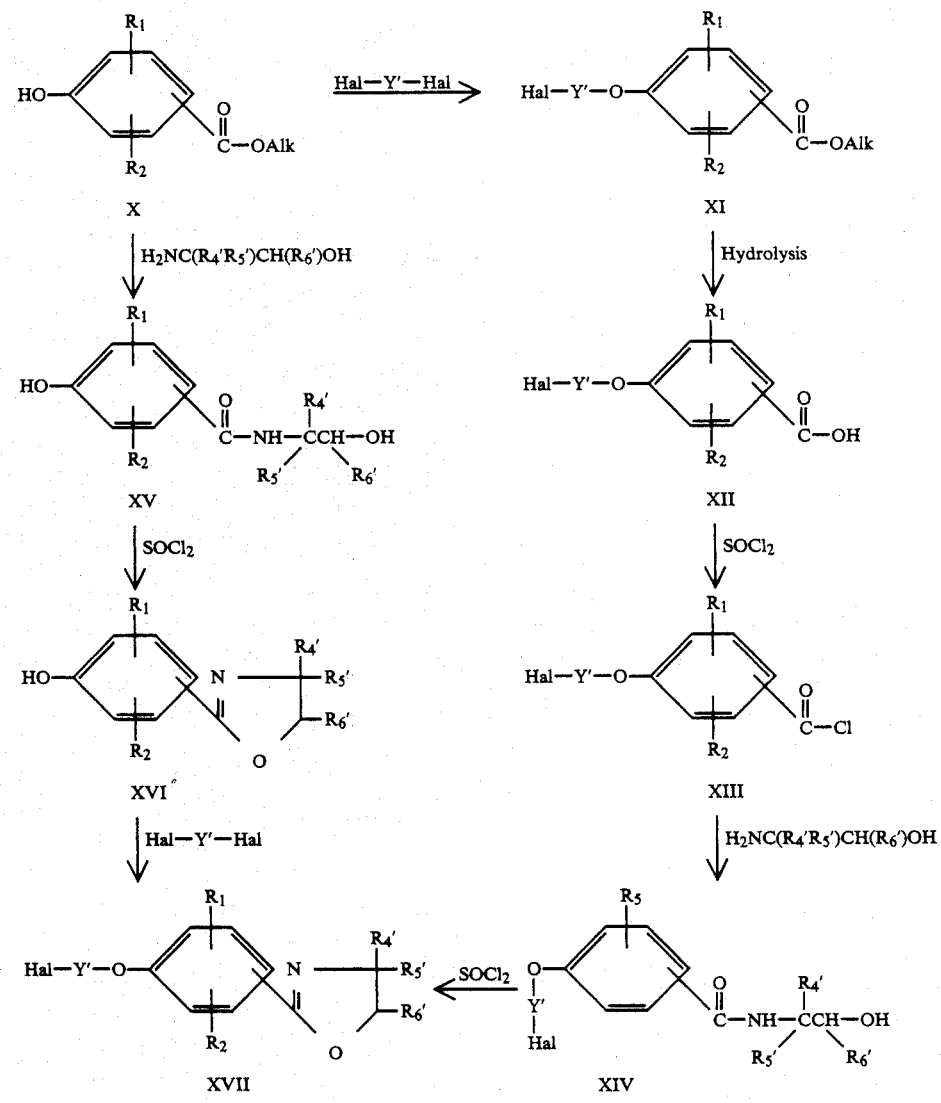

A hydroxybenzoate (X, Alk=lower-alkyl) in the presence of a base reacts with an alkylene dihalide to form a haloalkyl ether (XI). The ester groups is then hydrolyzed, preferably with a strong acid, to give the corresponding carboxylic acid (XII). The latter is converted to its acid chloride (XIII) which reacts with hydroxyethylamine or an alkylated or hydroxyalkylated derivative thereof to give an amide of the Formula XIV. The amide is then cyclized with thionyl chloride to give the desired intermediate of Formula invention.

EXAMPLE 1

(a) N-(2-Hydroxyethyl)-4-hydroxybenzamide [XV; $R_1$, $R_2$, $R_4'$, $R_5'$ and $R_6'$=H, OH at p-position]

A mixture of 80 g of methyl 4-hydroxybenzoate and 120 ml of ethanolamine was heated at 150° C. for five hours during which time 14.2 ml of methanol was distilled off. The excess ethanolamine was removed in vacuo, and the residue was treated with two 150 ml portions of chloroform. The chloroform was removed in vacuo and the residual oil dissolved in acetone from which the product crystallized to give 45.3 g of N-(2-hydroxyethyl)-4-hydroxybenzamide.

(b) 4,5-Dihydro-2-(4-hydroxyphenyl)oxazole [XVI; $R_1$, $R_2$, $R_4'$, $R_5'$ and $R_6'$=H, OH at p-position]

Thionyl chloride (160 ml) was added to 40 g of N-(2-hydroxyethyl)-4-hydroxybenzamide with evolution of gas. The reaction mixture was ultrasonicated for 1.75 hours, then cooled and diluted with ether. The resulting solid product was collected by filtration, washed with ether and dried overnight in a vacuum oven at 40° C. to give 42.5 g of 4,5-dihydro-2-(4-hydroxyphenyl)oxazole in the form of its hydrochloride salt.

(c) 2-(6-Bromohexyl)furan [V; Z=HC, Hal=Br, R' and $R_3'$=H, Y=$(CH_2)_6$]

n-Butyllithium solution in tetrahydrofuran (126 ml, 2.6M) was added dropwise to a solution of 22.4 g of furan in 200 ml of tetrahydrofuran at −25° to −28° C. After addition was complete, the mixture was stirred 4 hours at −15° C. and then cooled to −78° C. To this mixture was added a solution of 101.6 ml of 1,6-dibromohexane in 150 ml of tetrahydrofuran, and the reaction mixture was stirred and allowed to warm to room temperature overnight. The reaction mixture was quenched with 200 ml of saturated ammonium chloride solution and extracted with ether. The ether extracts were dried (MgSO$_4$) and concentrated to an oil (7.2 g containing 76% of desired product). The latter was distilled at 40 mm and the fraction boiling at 150°-153° C. was collected and used directly in the next reaction.

(d) 2-{4-[6-(2-Furanyl)hexyloxy]phenyl}-4,5-dihydrooxazole [IA; R, $R_1$, $R_2$, $R_3$, $R_4$, $R_5$, $R_6$ and $R_8$=H; Y=$(CH_2)_6$, dihydrooxazole group at p-position]

2-(6-Bromohexyl)furan (5.00 g) was added to a solution of 3.25 g sodium iodide in 50 ml acetonitrile, and the mixture was heated at reflux for 2.5 hours. The mixture was cooled to room temperature, 4.327 g 4-(4,5-dihydro-2-oxazolyl)phenol hydrochloride and 5.9 g potassium carbonate were added, and the reaction mixture refluxed for 24 hours. The reaction mixture was cooled and filtered, and the solid washed with acetone. The filtrate and washings were concentrated to dryness and the residue partitioned between ethyl acetate and aqueous potassium hydroxide. The ethyl acetate fraction was dried (magnesium sulfate) and concentrated to an oil which was chromatographed on silica gel using hexane—ethyl acetate 1:1 as eluant. There was thus obtained 3.3 g 2-{4-[6-(2-furanyl)hexyloxy]phenyl}-4,5-dihydrooxazole as a colorless solid, m.p. 74° C.

EXAMPLE 2

(a) 2-(7-Bromoheptyl)furan [V; Z=HC, Hal=Br, R' and $R_3'$=H, Y=$(CH_2)_7$] was prepared from furan and 1,7-dibromoheptane in accordance with the procedure of Example 1, part (c) and obtained as a liquid boiling at 75°-85° C. (0.03 mm).

(b) 2-{4-[7-(2-Furanyl)heptyloxy]phenyl}-4,5-dihydrooxazole [IA; R, $R_1$, $R_2$, $R_3$, $R_4$, $R_5$, $R_6$ and $R_8$=H; Y=$(CH_2)_7$, dihydrooxazole group at p-position] was prepared from 4-(4,5-dihydro-2-oxazolyl)phenol hydrochloride and 2-(7-brompentyl)furan in accordance with the procedure of Example 1, part (d), and obtained in the form of pale yellow crystals, m.p. 75°-77° C. (from ether).

EXAMPLE 3

(a) 4-(2-Furanyl)-1,4-butadiene-1,1-dicarboxylic acid

A mixture of 122.1 g of 2-furanacrolein, 225 g of malonic acid, 330 ml of pyridine and 0.5 ml of piperidine was stirred on a steam bath for 4 hours. The reaction mixture was concentrated in vacuo, 1 liter of water added, and the mixture aacidified with 6N hydrochloric acid. The yellow solid product (120 g) was collected, washed with water, dried and used directly in the next reaction.

(b) 5-(2-Furanyl)pentanoic acid

The acid from part (a) was dissolved in aqueous potassium hydroxide and hydrogenated in the presence of 2 g of palladium-on-carbon catalyst for 4 hours. The hydrogenated product was acidified, isolated and refluxed with 150 ml of pyridine for 11 hours to cause decarboxylation. The resulting product was isolated and distilled to give 60.4 g of 5-(2-furanyl)pentanoic acid, b.p. 105°-120° C. (0.07 mm).

(c) 5-(2-Furnayl)pentanol 5-(2-Furanyl)pentanoic acid (60.4 g) was reduced with 13.7 g of lithium aluminum hydride in 400 ml of tetrahydrofuran, heated at reflux for about 16 hours. The product was isolated and purified by distillation to give 51.4 g of 5-(2-furanyl)pentanol, b.p. 70°-73° C. (0.1 mm).

(d) 5-(2-Furanyl)pentanol acetate 5-(2-Furanyl)pentanol (81.8 g) was esterified with 100 ml of acetic anhydride and 200 mg of dimethylaminopyridine to give 97.0 g of the acetate ester, b.p. 74°-75° C. (0.1 mm).

(e) 5-(5-Acetyl-2-furanyl)pentanol acetate

To a mixture of 100 ml of trifluoroacetic anhydride and 100 ml of glacial acetic acid was added 89 g of 5-(2-furanyl)pentanol acetate in 100 ml of acetic acid. The reaction mixture was allowed to stand at room temperature for about 16 hours, then poured into water and extracted with methylene dichloride. The extracts were concentrated and the residue distilled to give 60.6 g of 5-(5-acetyl-2-furanyl)pentanol acetate, b.p. 120°-123° C. (0.05 mm).

(f) 5-(5-Acetyl-2-furanyl)pentanol 5-(5-Acetyl-2-furanyl)pentanol acetate (60.6 g) was hydrolyzed with 3 g of sodium methoxide in 900 ml of absolute methanol and the product isolated to give 37.3 g of 5-(5-acetyl-2-furanyl)pentanol, b.p. 132°-135° C. (0.1 mm).

(g) 2-(5-Chloropentyl)-5-acetylfuran [V; Z=$CH_3COC$, Hal=Cl, R' and $R_3'$=H, Y=$(CH_2)_5$]

5-(5-Acetyl-2-furanyl)pentanol (9.8 g), 13.1 g of triphenylphosphine and 100 ml of carbon tetrachloride were combined and heated at reflux for 4 hours. The reaction mixture was concentrated in vacuo, and the residue was dissolved in ether and filtered. The filtrate was concentrated and the residue distilled twice to give 2-(5-chloropentyl)-5-acetylfuran, b.p. 100°-102° C. (0.05 mm) in 60% yield.

(h) 2-{4-[5-(5-Acetyl-2-furanyl)pentyloxy]phenyl}-4,5-dihydrooxazole [IA; R, $R_1$, $R_2$, $R_3$, $R_4$, $R_5$ and $R_6$=H, $R_8$=CH$_3$CO, Y=(CH$_2$)$_5$, dihydrooxazole group at p-position] was prepared from 10.7 g of 2-(5-chloropentyl)-5-acetylfuran, 8.15 g of 4-(4,5-dihydro-2-oxazolyl)phenol, 10 g of potassium carbonate, 5 g of sodium iodide and 100 ml of acetone, heated at reflux for 24 hrs, and was obtained in 63% yield as a colorless solid, m.p. 125°–126° C. (from acetonitrile).

EXAMPLE 4

2-{4-[5-(5-Acetyl-2-furanyl)pentyloxy]-3-bromophenyl}-4,5-dihydrooxazole [IA; $R_1$=3-Br, R, $R_2$, $R_3$, $R_4$, $R_5$ and $R_6$=H, $R_8$=CH$_3$CO, Y=(CH$_2$)$_5$, dihydrooxaole group at p-position] was prepared from 2-(5-chloropentyl)-5-acetylfuran (Example 3g) and 2-bromo-4-(4,5-dihydro-2-oxazolyl)phenol according to the procedure of Example 3, part (h), and was obtained in the form of a tan solid, m.p. 91°–92° C. (from methanol).

EXAMPLE 5

(a)

3,5-Dichloro-4-hydroxy-N-(2-hydroxyethyl)benzamide [XV; $R_1$=3-Cl, $R_2$=5-Cl, $R_4'$, $R_5'$ and $R_6'$=H, OH at p-position]

A 2 L, 3 necked, round bottom flask was charged with 2-aminoethanol (240 gm; 3.93 moles) and heated to 80° C. Methyl 3,5-dichloro-4-hydroxybenzoate (432 gm; 1.96 moles) was added in portions through a powder funnel. The resulting amber solution was heated to 145° C. and the liberated methanol distilled into a Dean Stark trap. The reaction requires about 3.5 hrs. Upon completion, the solution was cooled to 90°–100° C. and dissolved in 1.95 L H$_2$O. The aqueous solution was cooled to 25° C., placed in an ice bath and made slightly acidic with concentrated hydrochloric acid (196 ml; 2.35 moles). The product precipitated and filtration afforded a white solid. After drying at 50° C. in a vacuum oven, the product darkened slightly. The crude material (384.4 gm; 78.8%) was ground and passed through a No. 20 mesh screen to produce 3,5-dichloro-4-hydroxy-N-(2-hydroxyethyl)benzamide as a cream colored solid (m.p. 174°–178° C.) which is suitable for use in the next step.

(b) 2,6-Dichloro-4-(4,5-dihydro-2-oxazolyl)phenol [XVI; $R_1$=2-Cl, $R_2$=6-Cl, $R_4'$, $R_5'$ and $R_6'$=H, OH at p-position]

3,5-Dichloro-4-hydroxy-N-(2-hydroxyethyl)benzamide (400 gm, 1.61 moles) was ground and sifted through a No. 20 mesh screen prior to use. To a stirred suspension of the above in 2.8 L isopropyl acetate was added thionyl chloride (285 gm, 2.41 moles) in a steady stream. An exotherm to 45°–50° C. developed and the gray suspension appeared lighter after a short time. After stirring 2.5 hr, the suspension was cooled to room temperature and filtered. The cake was rinsed with isopropyl acetate and dried in a vacuum oven at room temperature overnight. There was obtained 371 gm (86% yield) of 2,6-dichloro-4-(4,5-dihydro-2-oxazolyl)-phenol in the form of its hydrochloride salt, m.p. 189°–191° C., acceptable for use in the next step. The purified free base had the m.p. 195° C. (decompn.).

(c) 2-{3,5-Dichloro-4-[5-(2-furanyl)pentyloxy]phenyl}-4,5-dihydrooxazole [IA; $R_1$=3-Cl, $R_2$=5-Cl, R, $R_3$, $R_4$, $R_5$, $R_6$ and $R_8$=H, Y=(CH$_2$)$_5$), dihydrooxazole group at p-position] was prepared from 2.5 g 2,6-dichloro-4-(4,5-dihydro-2-oxazolyl)phenol (Example 5b) and 4 g 2-(5-bromopentyl)furan (prepared from furan and 1,5-dibromopentane) according to the procedure of Example 3, part (h), and was obtained in 90% yield (3.1 g) as an amber oil after chromatography on silica gel using ethyl acetate-hexane 1:1 as eluant.

EXAMPLE 6

2-}3,5-Dichloro-4-[5-(5-acetyl-2-furanyl)pentyloxy]-phenyl}-4,5-dihydrooxazole [IA; $R_1$=3-Cl, $R_2$=5-Cl, R, $R_3$, $R_4$, $R_5$ and $R_6$=H, $R_8$=CH$_3$CO, Y=(CH$_2$)$_5$, dihydrooxazole group at p-position] was prepared from 18 g 2,6-dichloro-4-(4,5-dihydro-2-oxazolyl)phenol (Example 5b) and 29 g 2-(5-bromopentyl)-5-actylfuran [prepared from 2-(5-bromopentyl)furan and p-toluenesulfonyl acetate (4-CH$_3$C$_6$H$_4$SO$_2$OCOCH$_3$)], and was obtained (19.2 g) as a colorless solid, m.p. 56°–58° C. after chromatography on silica and recrystallization from ether-hexane.

Further compounds are contemplated as follows:

2-{3,5-Dimethyl-4-[5-(2-furanyl)pentyloxy]phenyl}-4,5-dihydrooxazole [IA; $R_1$=3-CH$_3$, $R_2$=5-CH$_3$, R, $R_3$, $R_4$, $R_5$ and $R_8$=H, Y=(CH$_2$)$_5$, dihydrooxazole group at p-position], prepared from 2,6-dimethyl-4-(4,5-dihydro-2-oxazolyl)phenol and 2-(5-bromopentyl)furan.

2-{3,5-Dimethyl-4-[5-(5-acetyl-2-furanyl)pentyloxy]phenyl}-4,5-dihydrooxazole [IA; $R_1$=3-CH$_3$, $R_2$=5-CH$_3$, R, $R_3$, $R_4$, $R_5$ and $R_6$=H, $R_8$=CH$_3$CO, Y=(CH$_2$)$_5$, dihydrooxazole group at p-position], prepared from 2,6-dimethyl-4-(4,5-dihydro-2-oxazolyl)-phenol and 2-(5-bromopentyl)-5-acetylfuran.

2-{3,5-Dichloro-4-[5-(2-furanyl)pentyloxy]phenyl}-4,5-dihydro-4-methyloxazole [IA; $R_1$=3-Cl, $R_2$=5-Cl, $R_4$=CH$_3$; R, $R_3$, $R_5$, $R_6$ and $R_8$=H, Y=(CH$_2$)$_5$, dihydrooxazole group at p-position], prepared from 2,6-dichloro-4-(4,5-dihydro-4-methyl-2-oxazolyl)phenol and 2-(5-bromopentyl)furan.

2-{3,5-Dichloro-4-[5-(5-acetyl-2-furanyl)pentyloxy]phenyl}-4,5-dihydro-4-methyloxazole [IA; $R_1$=3-Cl, $R_2$=5-Cl, $R_4$=CH$_3$, R, $R_3$, $R_5$ and $R_6$=H, $R_8$=CH$_3$CO, Y=(CH$_2$)$_5$), dihydrooxazole group at p-position], prepared from 2,6-dichloro-4-(4,5-dihydro-4-methyl-2-oxazolyl)phenol and 2-(5-brompentyl)-5-acetylfuran.

2-{3,5-Dichloro-4-[5-(5-acetyl-2-furanyl)pentyloxy]phenyl}-4,5-dihydro-4-hydroxymethyloxazole (IA; $R_1$=3-Cl, $R_2$=5-Cl, $R_4$=CH$_2$OH, R, $R_3$, $R_5$ and $R_6$=H, $R_8$=CH$_3$CO, Y=(CH$_2$)$_5$, dihydrooxazole group at 4-position] prepared from 2,6-dichloro-4-(4,5-dihydro-4-hydroxymethyl-2-oxazolyl)phenol and 2-(5-bromopentyl)-5-acetylfuran.

Biological evaluation of compounds of Formulas I and III has shown that they possess antiviral activity. They are useful in inhibiting virus replication in vitro and are primarily active against picronaviruses, including enteroviruses, polioviruses, echovirus and coxsackie virus, and especially numerous strains of rhinoviruses. The in vitro testing of the compounds of the invention against picronaviruses showed that viral replication was inhibited at minimum inhibitory concentrations (MIC) ranging from about 0.003 to about 5 micrograms per milliliter.

The MIC values were determined by a standard plaque reduction assay as follows: HeLa (Ohio) cells in monolayers were infected at a concentration of virus to give approximately 80 plaques per monolayer in the virus control (no drug present). The compound to be tested was serially diluted and included in the agar-medium overlay and in some cases, during the adsorption period as well. The MIC was determined to be that concentration of compound which reduced the number of plques by 50% with respect to the untreated virus control.

In the standard test procedure, the compounds were tested against a panel of fifteen human rhinovirus (HRV) serotypes, namely HRV-2, -1A, -1B, -6, -14, -21, -22, -15, -25, -30, -50, -67, -89, -86 and -41. The MIC value for each rhinovirus serotype was determined, and the efficacy of each compound was determined in terms of $MIC_{50}$ and $MIC_{80}$ values, which is the concentration of the compound required to inhibit 50% and 80%, respectively, of the tested serotypes.

The following Table gives the testing results with the compounds of the invention.

|  | In vitro Activity | | |
| --- | --- | --- | --- |
|  | Polio 2 | Rhinovirus | |
| Example No. | MIC (μg/ml) | $MIC_{50}$ | $MIC_{80}$ |
| 1(d) | 0.9* | 4.8*[a] | |
| 2(b) | 0.09* | 3.5*[a] | |
| 3(h) | 0.3* | 0.15 | 0.36 |
| 4 | 2.7 | 0.12 | 0.37 |
| 5(c) | 12.5 | 0.46 | 2.29 |
| 6 | IA[b] | 0.12 | 0.29 |

*Compound present during adsorption and in the overlay media
[a]Against HRV-2 only
[b]Inactive The antiviral compositions are formulated for use by preparing a dilute solution or suspension in a pharmaceutically acceptable aqueous, organic or aqueous-organic medium for topical and parenteral administration by intravenous or intramuscular injection, or for intranasal or ophthalmic application; or are prepared in tablet, capsule, or aqueous suspension form with conventional excipients for oral administration.

We claim:

1. A compound of the formula

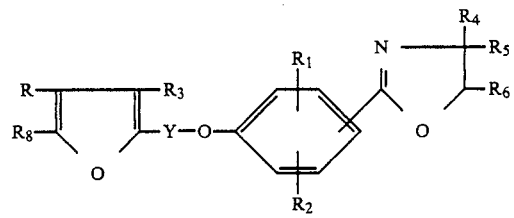

wherein:
Y is an alkylene bridge of 3 to 9 carbon atoms optionally interrupted by one or two oxygen atoms, by cyclohexyl, or by an olefinic linkage;
$R_1$ and $R_2$ are selected from the group consisting of hydrogen, lower-alkyl, lower-alkenyl, halogen, nitro, lower-alkoxy, lower-alkylthio, difluoromethyl, trifluoromethyl, amino, lower-alkanoylamino, di-lower-alkylamino, hydroxy, lower-alkenoyl, lower-alkanoyl, hydroxymethyl and carboxy;
R, $R_3$, $R_4$, $R_5$ and $R_6$ are each hydrogen or alkyl or hydroxyalkyl of 1–3 carbon atoms; and
$R_8$ is hydrogen or lower-alkanoyl;
or a pharmaceutically acceptable acid-addition salt thereof.

2. A compound according to claim 1 wherein Y is an alkylene bridge of 3 to 9 carbon atoms; $R_1$ and $R_2$ are selected from the group consisting of hydrogen, halogen and lower-alkyl; R, $R_3$, $R_4$, $R_5$ and $R_6$ are hydrogen; and the dihydrooxazolyl group is in the p-position of the phenyl ring with respect to the furan-substituted sidechain.

3. 2-{4-[6-(2-Furanyl)hexyloxy]phenyl]-4,5-dihydrooxazole, according to claim 2.

4. 2-{4-[7-(2-Furanyl(heptyloxy)]phenyl}-4,5-dihydrooxazole, according to claim 2.

5. 2-{4-[5-(5-Acetyl-2:furanyl)pentyloxy]phenyl}-4,5-dihydrooxazole, according to claim 2.

6. 2-{4-[5-(5-Acetyl-2-furanylpentyloxy]-2-bromophenyl}-4,5-dihydrooxazole, according to claim 2.

7. 2-{3,5-Dichloro-4-[5-(2-furanyl)pentyloxy]phenyl}-4,5-dihydrooxazole, according to claim 2.

8. 2-{3,5-Dichloro-4-[5-(5-acetyl-2-furanyl)pentyloxy]phenyl}-4,5-dihydrooxazole, according to claim 2.

9. A composition for combatting picornaviruses which comprises an antivirally effective amount of a compound according to claim 1 in admixture with a suitable carrier or diluent.

10. A method for combatting picornaviruses which comprises contacting the locus of said viruses with a composition according to claim 9.

* * * * *

UNITED STATES PATENT AND TRADEMARK OFFICE
CERTIFICATE OF CORRECTION

PATENT NO. : 4,861,791
DATED : August 29, 1989
INVENTOR(S) : Guy D. Diana & Philip M. Carabateas It is certified that error appears in the above-indentified patent and that said Letters Patent is hereby corrected as shown below:

Cover page and column 1, the title should read
-- DIHYDRO-OXAZOLYL SUBSTITUTED-PHENYL-ALIPHATIC-LOWER-ALKYLFURANS AND THEIR USE AS ANTIVIRAL AGENTS --.

Column 12, line 34, Claim 3, "phenyl]-" should read
-- phenyl}- --; line 36, Claim 4, "-(2-Furanyl(heptyloxy]"
should read -- -(2-Furanyl)heptyloxy] --; line 38, Claim 5,
"-(5-Acetyl-2:furanyl)" should read -- -(5-Acetyl-2-furanyl) --.

Signed and Sealed this

Thirteenth Day of July, 1993

Attest:

MICHAEL K. KIRK

*Attesting Officer*   Acting Commissioner of Patents and Trademarks